United States Patent [19]

Wu et al.

[11] Patent Number: 6,051,745
[45] Date of Patent: Apr. 18, 2000

[54] SILICOALUMINOPHOSPHATE MATERIAL, A METHOD OF MAKING SUCH IMPROVED MATERIAL AND THE USE THEREOF IN THE CONVERSION OF OXYGENATED HYDROCARBONS TO OLEFINS

[75] Inventors: An-hsiang Wu; Ralph J. Melton, both of Bartlesville; Charles A. Drake, Nowata, all of Okla.

[73] Assignee: Phillips Petroleum Company, Bartlesville, Okla.

[21] Appl. No.: 09/262,799

[22] Filed: Mar. 4, 1999

[51] Int. Cl.[7] .............................. C07C 1/00; B01J 24/24; B01J 27/182
[52] U.S. Cl. ......................... 585/638; 585/639; 585/640; 502/200; 502/232; 502/208; 502/214; 502/240; 502/263
[58] Field of Search .................................... 502/200, 232, 502/208, 214, 240, 263; 585/638, 639, 640

[56] References Cited

U.S. PATENT DOCUMENTS

| | | | |
|---|---|---|---|
| 4,440,871 | 4/1984 | Lok et al. | 502/214 |
| 4,861,938 | 8/1989 | Lewis et al. | 585/640 |
| 5,185,310 | 2/1993 | Degnan et al. | 502/214 |
| 5,248,647 | 9/1993 | Barger | 502/214 |
| 5,475,182 | 12/1995 | Janssen | 585/640 |
| 5,609,843 | 3/1997 | Wendelbo | 423/306 |
| 5,663,471 | 9/1997 | Kvisle et al. | 585/639 |
| 5,888,921 | 3/1997 | Tsang et al. | 502/64 |

*Primary Examiner*—Elizabeth D. Wood
*Attorney, Agent, or Firm*—Jeffrey R. Anderson

[57] ABSTRACT

A catalyst system comprising a nitrided silicoaluminophosphate, and a method of preparing such catalyst system which comprises nitriding a silicoaluminophosphate, are disclosed. The thus-obtained catalyst system is employed as a catalyst in the conversion of a hydrocarbon feedstock comprising oxygenated hydrocarbons to olefins.

74 Claims, No Drawings

SILICOALUMINOPHOSPHATE MATERIAL, A METHOD OF MAKING SUCH IMPROVED MATERIAL AND THE USE THEREOF IN THE CONVERSION OF OXYGENATED HYDROCARBONS TO OLEFINS

BACKGROUND OF THE INVENTION

The invention relates to catalyst systems useful in hydrocarbon upgrading processes and to methods for their production and use. In another aspect, this invention relates to processes for converting oxygenated hydrocarbons to $C_2$–$C_4$ olefins with an increase in olefin selectivity and a reduction in coke formation resulting from the conversion of such oxygenated hydrocarbons in the presence of such catalyst systems. The term "oxygenated hydrocarbons" as employed herein comprises hydrocarbons containing aliphatic moieties such as, but not limited to, alcohols, halides, mercaptans, sulfides, amines, ethers, and carbonyl compounds (aldehydes, ketones, carboxylic acids and the like) or mixtures thereof.

It is known to convert oxygenated hydrocarbons to olefins in the presence of catalysts which contain a silicoaluminophosphate (SAPO), as is described in U.S. Pat. Nos. 4,861,938, 5,475,182, 5,248,647 and 5,663,471, each incorporated herein by reference.

One concern with the use of SAPO catalysts in the conversion of oxygenated hydrocarbons to olefins is the excessive production of coke during the conversion reaction. Coke formed during the SAPO catalyzed conversion of oxygenated hydrocarbons tends to cause catalyst deactivation. It is desirable to improve processes for the conversion of oxygenated hydrocarbons to olefins by minimizing the amount of coke formed during such processes. It is also desirable to have a SAPO catalyst that is useful in producing significant quantities of olefin conversion products.

SUMMARY OF THE INVENTION

It is an object of this invention to provide an improved SAPO material which when used in the conversion of oxygenated hydrocarbons results in increased olefin yield and decreased coke production.

A yet further object of this invention is to provide a method for making an improved SAPO material having such desirable properties as providing for increased olefin yield and decreased coke production when used in the conversion of oxygenated hydrocarbons.

Another object of this invention is to provide an improved process for the conversion of oxygenated hydrocarbons in which the yield of olefins is increased and the production of coke is decreased.

The inventive catalyst system comprises a nitrided SAPO. The inventive catalyst system can be prepared by nitriding the SAPO under suitable conditions. The inventive catalyst system can be used in the conversion of an oxygenated hydrocarbon to olefins by contacting, under conversion conditions, a hydrocarbon feedstock containing an oxygenated hydrocarbon with the inventive catalyst system.

Other objects and advantages of the invention will become apparent from the detailed description and the appended claims.

DETAILED DESCRIPTION OF THE INVENTION

The SAPO material used in preparing the inventive catalyst system can be any SAPO that is effective in the conversion of oxygenated hydrocarbons to olefins when contacted under conversion conditions with oxygenated hydrocarbons.

SAPO catalysts exhibit properties of both aluminosilicate zeolites and aluminophosphates. The SAPO's have a three-dimensional microporous crystal framework structure of $PO_2$, $AlO_2$ and $SiO_2$ tetrahedral units. The chemical composition (anhydrous) is:

wherein "R" represents at least one organic templating agent present in the intracrystalline pore system: "m" represents the moles of "R" present per mole of $(Si_xAl_yP_z)O_2$ and has a value of from zero to 0.3, the maximum value in each case depending upon the molecular dimensions of the templating agent and the available void volume of the pore system of the particular SAPO species involved, and "x", "y" and "z" represent the mole fractions of silicon, aluminum and phosphorus, respectively.

Examples of such templating agents include, but are not limited to, tetramethylammonium hydroxide, tetraethylammonium hydroxide, and tetrapropylammonium hydroxide. Further details relating to the formation of SAPO compositions, including molar amounts of each oxide source, can be found in the Lok et al. U.S. Pat. No. 4,440,871, the entire disclosure of which is expressly incorporated herein by reference.

SAPO compositions useful in the present invention include, but are not limited to, SAPO-4, SAPO-5, SAPO-11, SAPO-16, SAPO-17, SAPO-20, SAPO-31, SAPO-34, SAPO-35, SAPO-37, SAPO-40, SAPO-41, SAPO-42, and SAPO-44. The presently more preferred SAPO is SAPO-34.

The SAPO can be combined or mixed with a binder material in a liquid such as water or a hydrocarbon, by any means known to one skilled in the art such as stirring, blending, kneading, or extrusion, following which the resulting mixture can be dried in air.

The SAPO or the mixture can be calcined at a temperature in the range of from about 250° C. to about 1000° C., preferably from about 350° C. to about 750° C., and most preferably from 450° C. to 650° C., for a time period in the range of from about 0.1 hour to about 30 hours, preferably from about 2 hours to about 20 hours, and most preferably from 3 hours to 15 hours, and under any pressures that accommodate the temperatures, preferably atmospheric pressure.

Any binders known to one skilled in the art for use with a SAPO are suitable for use herein. Examples of suitable binders include, but are not limited to, aluminas such as for example α-alumina and γ-alumina; silicas; alumina-silica; aluminum phosphate; aluminum chlorohydrate; clays such, as kaolinite, halloysite, vermiculite, chlorite, attapulgite, smectite, montmorillonite, illite, saconite, sepiolite, palygorskite, and combinations of any two or more thereof. Because these binders are well known to one skilled in the art, description of which is omitted herein. The presently preferred binder, if employed, is silica.

The SAPO, or SAPO-binder mixture, can be extruded into pellets or tablets by any method known to those skilled in the art.

The SAPO, whether bound in a SAPO-binder mixture, and whether or not extruded, can be nitrided by any suitable means or method known in the art for nitriding SAPOs. A presently preferred method is to contact the SAPO with a nitrogen-and-hydrogen containing compound under conditions suitable for nitriding SAPOs. The nitrogen-andhydrogen containing compound is preferably a gas and can include, but is not limited to, at least one organonitrogen compound, ammonia and a gas mixture comprising hydrogen and at least one nitrogen oxide.

Examples of suitable organonitrogen compounds include, but are not limited to, amines, pyrrole, pyridine and mixtures of any two or more thereof.

Examples of suitable nitrogen oxides include, but are not limited to, nitrous oxide, nitric oxide, nitrogen trioxide, dinitrogen tetroxide, nitrogen dioxide, dinitrogen pentoxide, trinitrogen tetroxide, and mixtures of any two or more thereof.

The SAPO is preferably contacted with the nitrogen-and-hydrogen containing compound by passing the nitrogen-and-hydrogen containing compound over the SAPO in the presence of hydrogen at a temperature in the range of from about 200° C. to about 1,200° C., for a time period in the range of from about 0.1 hour to about 30 hours.

Any suitable hydrocarbon feedstock, which comprises oxygenated hydrocarbons, can be used as the feed to be contacted with the inventive catalyst system under suitable process conditions for obtaining a reaction product comprising olefins. The aliphatic moieties of the oxygenated hydrocarbons preferably contain in the range of from about 1 to about 10 carbon atoms, and more preferably, contain from about 1 to about 4 carbon atoms. Representative oxygenated hydrocarbons include, but are not limited to, lower straight or branched chain alcohols, their unsaturated counterparts and the nitrogen, halogen and sulfur analogues of such. Examples of suitable compounds include, but are not limited to, methanol, isopropanol, n-propanol, ethanol, fuel alcohols, methyl mercaptan, methyl sulfide, methyl amine, dimethyl ether, ethyl mercaptan, ethyl chloride, diethyl ether, methylethyl ether, formaldehyde, dimethyl ketone, acetic acid, n-alkyl amines, n-alkyl halides and n-alkyl sulfides having n-alkyl groups of 3 to 10 carbon atoms, and mixtures of any two or more thereof. The preferred oxygenated hydrocarbon is methanol.

The hydrocarbon feedstock can be contacted, by any suitable manner, with the inventive catalyst system described herein contained within a reaction zone. The contacting step can be operated as a batch process step or, preferably, as a continuous process step. In the latter operation, a solid catalyst bed or a moving catalyst bed or a fluidized catalyst bed can be employed. Any of these operational modes have advantages and disadvantages, and those skilled in the art can select the one most suitable for a particular feed and catalyst.

The contacting step is preferably carried out within a conversion reaction zone, wherein is contained the inventive catalyst system, and under reaction conditions that suitably promote the formation of olefins, preferably light olefins, from at least a portion of the oxygenated hydrocarbons of the hydrocarbon feedstock. The reaction temperature of the contacting step is more particularly in the range of from about 200° C. to about 800° C., preferably from about 250° C. to about 750° C. and, most preferably, from 300° C. to 700° C. The contacting pressure can range from about 0 psig to about 500 psig, preferably, from about atmospheric pressure to about 450 psig and, most preferably, from atmospheric pressure to 400 psig.

The flow rate at which the hydrocarbon feedstock is charged to the conversion reaction zone is such as to provide a weight hourly space velocity ("WHSV") in the range of from exceeding 0 hour$^{-1}$ upwardly to about 1000 hours$^{-1}$. The term "weight hourly space velocity", as used herein, shall mean the numerical ratio of the rate at which a hydrocarbon feedstock is charged to the conversion reaction zone in pounds per hour divided by the pounds of catalyst contained in the conversion reaction zone to which the hydrocarbon is charged. The preferred WHSV of the feed to the conversion reaction zone or contacting zone can be in the range of from about 0.25 hour$^{-1}$ to about 250 hours$^{-1}$ and, most preferably, from 0.5 hour$^{-1}$ to 100 hours$^{-1}$.

The olefin production process is generally carried out in the presence of one or more inert diluents which can be present in an amount in the range of from about 1 to about 99 molar percent, based on the total number of moles of all feed and diluent components fed to the reaction zone. Suitable diluents include, but are not limited to, helium, argon, nitrogen, carbon monoxide, carbon dioxide, hydrogen, water, paraffins, hydrocarbons (such as methane and the like), aromatic compounds, and mixtures of any two or more thereof. The presently preferred diluent is water.

The following examples are presented to further illustrate this invention and are not to be construed as unduly limiting its scope.

EXAMPLE 1

This example illustrates the preparation of catalysts which were subsequently tested as catalysts in the conversion of a hydrocarbon feedstock comprising methanol to olefins.

Catalyst A (Control)

A 10 gram quantity of a commercially available SAPO-34 catalyst (provided by UOP, LLC, Des Plaines, Ill. under product designation SAPO-34) was mixed with a 10 gram quantity of a colloidal silica solution (manufactured by DuPont under product designation Ludox® AS-40). The formed mixture was then extruded into ¹⁄₁₆" diameter pellets and dried at room temperature followed by calcining at a temperature of about 538° C. for 6 hours.

Catalyst B (Invention)

A 4.36 gram quantity of Catalyst A was nitrided by contact with ammonia gas. The ammonia gas was passed over the 4.36 gram quantity of Catalyst A at a flow rate of 200 mL/min and at a temperature of 750° C. for 2 hours.

EXAMPLE 2

This example illustrates the use of the catalysts described in Example 1 in the conversion of methanol to olefins.

In Run 1, a 1.78 gram quantity of Catalyst A described in Example 1 was placed into a stainless steel tube reactor (length: about 18 inches; inner diameter: about 0.5 inch). The steel reactor tube was heated to about 448° C. The reactor pressure was about 0 psig. A methanol/water feed, comprising 20 mole % methanol and 80 mole % water, was introduced to the reactor tube at a flow rate of 25 mL/hour to yield a methanol WHSV of 4.0. The product was analyzed by means of a gas chromatograph. Test data results obtained after 7.2 hours on stream are summarized in the Table.

In Run 2, a 1.92 gram quantity of Catalyst B described in Example 1 was placed into a stainless steel tube reactor (length: about 18 inches; inner diameter: about 0.5 inch). The steel reactor tube was heated to about 449° C. The reactor pressure was about 0 psig. A methanol/water feed, comprising 20 mole % methanol and 80 mole % water, was introduced to the reactor tube at a flow rate of 25 mL/hour to yield a methanol WHSV of 3.7. The product was analyzed by means of a gas chromatograph. Test data results, obtained after 7.0 hours on stream are summarized in the Table.

TABLE

| Run | Catalyst | Methanol Conversion Wt. % | $\Sigma C_2^= - C_4^=$ Selectivity | Coke Wt. %/hour |
|---|---|---|---|---|
| 1 | A (control) | 100 | 96.9 | 1.5 |
| 2 | B (invention) | 100 | 98.0 | 0.72 |

The test data presented in the Table show that use of the inventive Catalyst B in Run 2 resulted in an increased $C_2^=$ to $C_4^=$ selectivity and a considerable decrease in coke production as compared to the use of control Catalyst A in Run 1.

Inventive Run 2 demonstrated a 1.1% increase in $C_2^=$ to $C_4^=$ selectivity and a 52% decrease in coke production over control Run 1.

Reasonable variations, modifications, and adaptations can be made within the scope of the disclosure and the appended claims without departing from the scope of this invention.

That which is claimed is:

1. A catalyst system comprising a nitrided silicoaluminophosphate.

2. A catalyst system as recited in claim 1 wherein said silicoaluminophosphate is SAPO-34.

3. A catalyst system as recited in claim 1 wherein said silicoaluminophosphate is calcined prior to being nitrided.

4. A catalyst system as recited in claim 3 wherein said silicoaluminophosphate is calcined at a temperature in the range of from about 250° C. to about 1000° C. for a time period in the range of from about 0.1 hour to about 30 hours.

5. A catalyst system as recited in claim 1 wherein said silicoaluminophosphate is nitrided with a nitrogen-and-hydrogen containing substance at a temperature in the range of from about 200° C. to about 1200° C. for a time period in the range of from about 0.1 hour to about 30 hours.

6. A catalyst system as recited in claim 5 wherein said nitrogen-and-hydrogen containing substance comprises at least one organonitrogen compound.

7. A catalyst system as recited in claim 5 wherein said nitrogen-and-hydrogen containing substance comprises a mixture of hydrogen and at least one nitrogen oxide.

8. A catalyst system as recited in claim 5 wherein said nitrogen-and-hydrogen containing substance comprises ammonia.

9. A method of preparing a catalyst system which comprises nitriding a silicoaluminophosphate thereby forming a nitrided silicoaluminophosphate.

10. A method in accordance with claim 9 wherein said silicoaluminophosphate is SAPO-34.

11. A method in accordance with claim 9 wherein said nitriding of said silicoaluminophosphate is with a nitrogen-and-hydrogen containing substance at a temperature in the range of from about 200° C. to about 1200° C. for a time period in the range of from about 0.1 hour to about 30 hours.

12. A method in accordance with claim 11 wherein said nitrogen-and-hydrogen containing substance comprises at least one organonitrogen compound.

13. A method in accordance with claim 11 wherein said nitrogen-and-hydrogen containing substance comprises a mixture of hydrogen and at least one nitrogen oxide.

14. A method in accordance with claim 11 wherein said nitrogen-and-hydrogen containing substance comprises ammonia.

15. A method of preparing a catalyst system which comprises the steps of:

(a) mixing a silicoaluminophosphate with a binder thereby forming a mixture; and (b) nitriding said mixture thereby forming a nitrided mixture.

16. A method in accordance with claim 15 wherein said silicoaluminophosphate is SAPO-34.

17. A method in accordance with claim 15 wherein said binder is silica.

18. A method in accordance with claim 15 characterized further to include the step of:

(c) extruding said mixture produced by step (a) prior to performing step (b).

19. A method in accordance with claim 15 wherein said nitriding of step (b) comprises contacting said mixture with a nitrogen-and-hydrogen containing substance at a temperature in the range of from about 200° C. to about 1200° C. for a time period in the range of from about 0.1 hour to about 30 hours.

20. A method in accordance with claim 19 wherein said nitrogen-and-hydrogen containing substance comprises at least one organonitrogen compound.

21. A method in accordance with claim 19 wherein said nitrogen-and-hydrogen containing substance comprises a mixture of hydrogen and at least one nitrogen oxide.

22. A method in accordance with claim 19 wherein said nitrogen-and-hydrogen containing substance comprises ammonia.

23. A method of preparing a catalyst system which comprises the steps of:

(a) mixing SAPO-34 with silica thereby forming a mixture;

(b) extruding said mixture thereby forming an extruded mixture; and (c) nitriding said extruded mixture with a nitrogen-and-hydrogen containing substance comprising a gas selected from the group consisting of at least one organonitrogen compound, a mixture of at least one nitrogen oxide and hydrogen, and ammonia, at a temperature in the range of from about 200° C. to about 1200° C. for a time period in the range of from about 0.1 hour to about 30 hours thereby forming a nitrided mixture.

24. A process for converting at least a portion of a hydrocarbon feedstock comprising at least one oxygenated hydrocarbon to at least one olefin which comprises contacting said hydrocarbon feedstock at conversion conditions with the catalyst system of claim 1.

25. A process as recited in claim 24 wherein said conversion conditions include a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

26. A process as recited in claim 24 wherein said at least one oxygenated hydrocarbon comprises methanol.

27. A process for converting at least a portion of a hydrocarbon feedstock comprising at least one oxygenated hydrocarbon to at least one olefin which comprises contacting said hydrocarbon feedstock at conversion conditions with the catalyst system of claim 2.

28. A process as recited in claim 27 wherein said conversion conditions include a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

29. A process as recited in claim 27 wherein said at least one oxygenated hydrocarbon comprises methanol.

30. A process for converting at least a portion of a hydrocarbon feedstock comprising at least one oxygenated hydrocarbon to at least one olefin which comprises contacting said hydrocarbon feedstock at conversion conditions with the catalyst system of claim 3.

31. A process as recited in claim 30 wherein said conversion conditions include a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

32. A process as recited in claim 30 wherein said at least one oxygenated hydrocarbon comprises methanol.

33. A process for converting at least a portion of a hydrocarbon feedstock comprising at least one oxygenated hydrocarbon to at least one olefin which comprises contacting said hydrocarbon feedstock at conversion conditions with the catalyst system of claim 4.

34. A process as recited in claim 33 wherein said conversion conditions include a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

35. A process as recited in claim 33 wherein said at least one oxygenated hydrocarbon comprises methanol.

36. A process for converting at least a portion of a hydrocarbon feedstock comprising at least one oxygenated hydrocarbon to at least one olefin which comprises contacting said hydrocarbon feedstock at conversion conditions with the catalyst system of claim 5.

37. A process as recited in claim 36 wherein said conversion conditions include a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

38. A process as recited in claim 36 wherein said at least one oxygenated hydrocarbon comprises methanol.

39. A process for converting at least a portion of a hydrocarbon feedstock comprising at least one oxygenated hydrocarbon to at least one olefin which comprises contacting said hydrocarbon feedstock at conversion conditions with the catalyst system of claim 6.

40. A process as recited in claim 39 wherein said conversion conditions include a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

41. A process as recited in claim 39 wherein said at least one oxygenated hydrocarbon comprises methanol.

42. A process for converting at least a portion of a hydrocarbon feedstock comprising at least one oxygenated hydrocarbon to at least one olefin which comprises contacting said hydrocarbon feedstock at conversion conditions with the catalyst system of claim 7.

43. A process as recited in claim 42 wherein said conversion conditions include a temperature in the range of from about 200° C. to about 800° C., a pressure in the range of from about 0 psig to about 500 psig, and a weight hourly space velocity in the range of from about 0.01 hours$^{-1}$ to about 1000 hours$^{-1}$.

44. A process as recited in claim 42 wherein said at least one oxygenated hydrocarbon comprises methanol.

45. A process for converting at least a portion of a hydrocarbon feedstock comprising at least one oxygenated hydrocarbon to at least one olefin which comprises contacting said hydrocarbon feedstock at conversion conditions with the catalyst system of claim 8.

46. A process as recited in claim 45 wherein said conversion conditions include a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

47. A process as recited in claim 45 wherein said at least one oxygenated hydrocarbon comprises methanol.

48. A process for converting at least a portion of a hydrocarbon feedstock comprising at least one oxygenated hydrocarbon to at least one olefin which comprises contacting said hydrocarbon feedstock at conversion conditions with a catalyst system prepared by the method of claim 15.

49. A process as recited in claim 48 wherein said conversion conditions include a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

50. A process as recited in claim 48 wherein said at least one oxygenated hydrocarbon comprises methanol.

51. A process for converting at least a portion of a hydrocarbon feedstock comprising at least one oxygenated hydrocarbon to at least one olefin which comprises contacting said hydrocarbon feedstock at conversion conditions with a catalyst system prepared by the method of claim 16.

52. A process as recited in claim 51 wherein said conversion conditions include a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

53. A process as recited in claim 51 wherein said at least one oxygenated hydrocarbon comprises methanol.

54. A process for converting at least a portion of a hydrocarbon feedstock comprising at least one oxygenated hydrocarbon to at least one olefin which comprises contacting said hydrocarbon feedstock at conversion conditions with a catalyst system prepared by the method of claim 17.

55. A process as recited in claim 54 wherein said conversion conditions include a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

56. A process as recited in claim 54 wherein said at least one oxygenated hydrocarbon comprises methanol.

57. A process for converting at least a portion of a hydrocarbon feedstock comprising at least one oxygenated hydrocarbon to at least one olefin which comprises contacting said hydrocarbon feedstock at conversion conditions with a catalyst system prepared by the method of claim 18.

58. A process as recited in claim 57 wherein said conversion conditions include a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

59. A process as recited in claim 57 wherein said at least one oxygenated hydrocarbon comprises methanol.

60. A process for converting at least a portion of a hydrocarbon feedstock comprising at least one oxygenated hydrocarbon to at least one olefin which comprises contacting said hydrocarbon feedstock at conversion conditions with a catalyst system prepared by the method of claim 19.

61. A process as recited in claim 60, wherein said conversion conditions include a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

62. A process as recited in claim 60 wherein said at least one oxygenated hydrocarbon comprises methanol.

63. A process for converting at least a portion of a hydrocarbon feedstock comprising at least one oxygenated hydrocarbon to at least one olefin which comprises contacting said hydrocarbon feedstock at conversion conditions with a catalyst system prepared by the method of claim 20.

64. A process as recited in claim 63 wherein said conversion conditions include a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

65. A process as recited in claim 63 wherein said at least one oxygenated hydrocarbon comprises methanol.

66. A process for converting at least a portion of a hydrocarbon feedstock comprising at least one oxygenated hydrocarbon to at least one olefin which comprises contacting said hydrocarbon feedstock at conversion conditions with a catalyst system prepared by the method of claim 21.

67. A process as recited in claim 66, wherein said conversion conditions include a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

68. A process as recited in claim 66, wherein said at least one oxygenated hydrocarbon comprises methanol.

69. A process for converting at least a portion of a hydrocarbon feedstock comprising at least one oxygenated hydrocarbon to at least one olefin which comprises contacting said hydrocarbon feedstock at conversion conditions with a catalyst system prepared by the method of claim 22.

70. A process as recited in claim 69 wherein said conversion conditions include a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

71. A process as recited in claim 69 wherein said at least one oxygenated hydrocarbon comprises methanol.

72. A process for converting at least a portion of a hydrocarbon feedstock comprising at least one oxygenated hydrocarbon to at least one olefin which comprises contacting said hydrocarbon feedstock at conversion conditions with a catalyst system prepared by the method of claim 23.

73. A process as recited in claim 72 wherein said conversion conditions include a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

74. A process as recited in claim 72 wherein said at least one oxygenated hydrocarbon comprises methanol.

* * * * *